(12) United States Patent
Kumar et al.

(10) Patent No.: US 6,559,335 B2
(45) Date of Patent: May 6, 2003

(54) PROCESS FOR THE PREPARATION OF 3-ARYL-2-HYDROXY PROPANOIC ACID

(75) Inventors: Potlapally Rajender Kumar, Ameerpet (IN); Siripragada Mahender Rao, Ameerpet (IN); Kotra Narasimha Murthy, Ameerpet (IN); Sirisilla Raju, Ameerpet (IN); Mamillapalli Ramabhadra Sarma, Ameerpet (IN); Gaddam Om Reddy, Ameerpet (IN)

(73) Assignee: Dr. Reddy's Laboratories Limited, Hyderabad (IN)

( * ) Notice: Subject to any disclaimer, the term of this patent is extended or adjusted under 35 U.S.C. 154(b) by 30 days.

(21) Appl. No.: 09/836,559

(22) Filed: Apr. 17, 2001

(65) Prior Publication Data

US 2002/0177726 A1 Nov. 28, 2002

(51) Int. Cl.$^7$ ................................. C07C 69/76
(52) U.S. Cl. ................... 560/61; 560/55; 560/60; 560/75
(58) Field of Search ............... 560/60, 55, 75; 569/61

(56) References Cited

U.S. PATENT DOCUMENTS 5,747,448 A * 5/1998 Ohyama et al. ............... 514/11

FOREIGN PATENT DOCUMENTS

| WO | 9401420 | 1/1994 |
|---|---|---|
| WO | 9517394 | 6/1995 |
| WO | 9741097 | 11/1997 |
| WO | 9962870 | 12/1999 |
| WO | 9962871 | 12/1999 |
| WO | 9962872 | 12/1999 |
| WO | 0026200 | 5/2000 |
| WO | 0111072 | 2/2001 |
| WO | 0111073 | 2/2001 |

OTHER PUBLICATIONS

Miklos Bodanszky et al., "The Practice of Peptide Synthesis", 2nd Ed., (1994), pp. 50–51.*
Theophil Eicher et al, "Bryophyte Constituents; 7: New Synthesis of (+)–Rosmarinic Acid and Related Compounds", Syn., (1996), pp. 755–762.*
David E. Bogucki et al, "A non–enzymatic synthesis of (S)–(–)–rosmarinic acid and a study of a biomimetic route to (+)–rabdosiin", Can. J. Chem., vol. 75 (1997), pp. 1783–1794.*

* cited by examiner

Primary Examiner—Alan L. Rotman
Assistant Examiner—Taylor V Oh
(74) Attorney, Agent, or Firm—Ladas & Parry

(57) ABSTRACT

The present invention relates to an improved process for the preparation of 3-aryl-2-hydroxy propanoic acid derivatives of the formula (1)

(1)

useful as an intermediate for the preparation of many pharmaceutically active compounds.

20 Claims, No Drawings

PROCESS FOR THE PREPARATION OF 3-ARYL-2-HYDROXY PROPANOIC ACID

FIELD OF THE INVENTION

The present invention relates to an improved process for the preparation of 3-aryl-2-hydroxy propanoic acid derivatives of the formula (1)

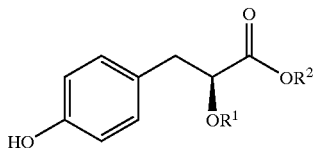

(1)

useful as an intermediate for the preparation of many pharmaceutically active compounds.

BACKGROUND OF INVENTION

The process for the preparation of 3-aryl-2-hydroxy propanoic acid, its derivatives and analogs exhibiting various pharmacological actives have been described in U.S. Pat. Nos. 5,232,945, 5,306,726, WO 91/11999, DE 1,948,373, DE. 2,033,959, DE 2,014,479, DE 1,668,938, WO 91/19702, WO 92/0252, WO 96/04260, WO 96/0426, WO 95/17394. In addition, these compounds are considered to be useful for treating certain eating disorders, in particular the regulation of appetite and food intake in subjects suffering from disorders associated with eating such as anorexia nervosa and disorders associated with overeating such as obesity and anorexia bulimia.

3-Aryl-2-hydroxy propanoic acid derivatives are also used as sweetening agent (Gries et.al. EP 55,689 (1982)), also in photosensitive materials (Komamura et.al. JP 6022850) and also in liquid crystals (Grey et.al. WO 88/02390).

It is also a part of sesquiterpene lactone glycoside isolated from *Crepis tectorium* (Kisiel Wanda et.al. Phytochemistry, 2403, 28 (9) (1989)]. It is also part of Aeruginorins 102A and B, a new class of Thrombin inhibitors from the *Cyanobacterium Microcystis vindis.*

3-Aryl-2-hydroxy propionic acid is prepared by several methods reported in the literature.

Hisashi Matruda, et.al., Tet. 52 (46) 14501 (1996)

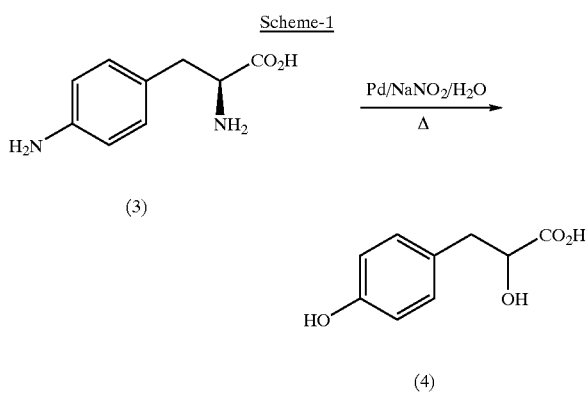

In our WO publication No. 00/26200 we have described process for preparing the compound of formula (1). The reaction schemes are shown below:

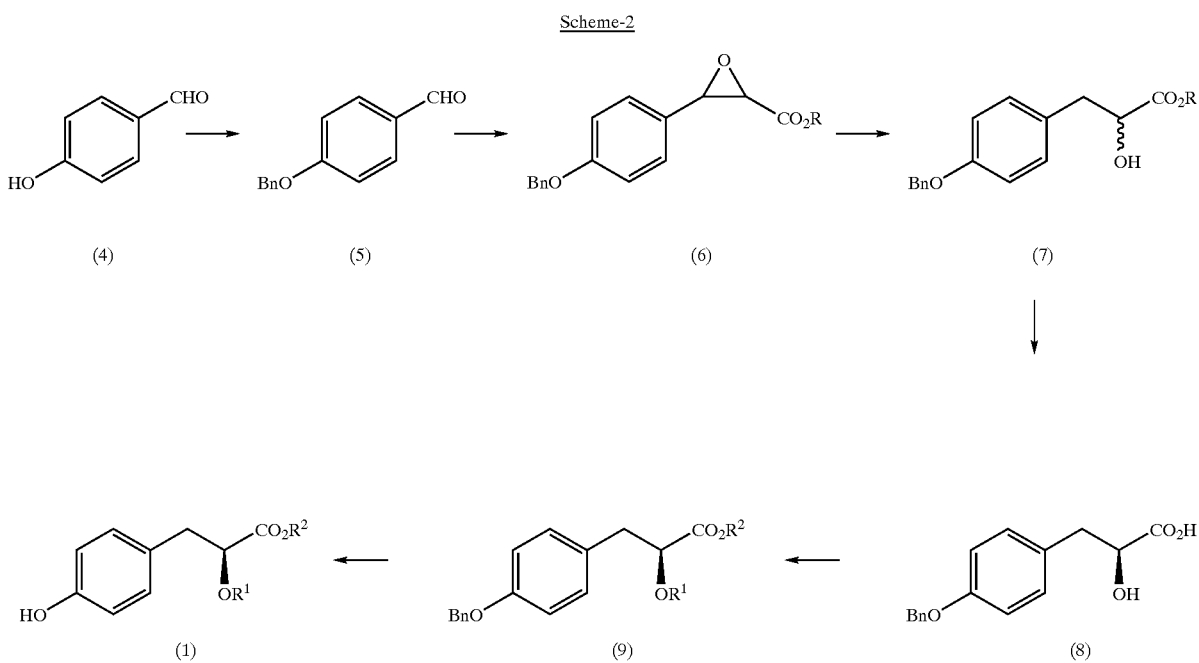

Though it is convergent synthetic method, the compound of formula (7) is produced in racemic mixture, which has to be resolved to get the optically pure material.

Scheme-3

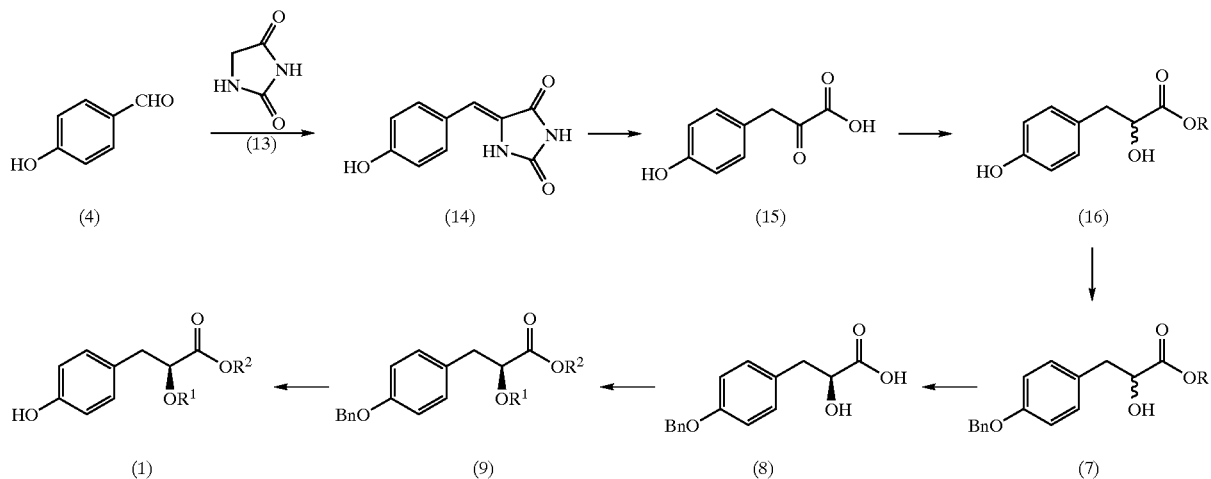

In this process too the resolution has to be carried out for compound of formula (7).

Scheme-4

(10), (11), (8), (9), (1)

Objective of Present Invention

The main objective of the present invention is to provide a simple and robust process for the preparation of the compound of formula (1) with high chemical and chiral purity.

Another objective of the present invention is to produce pure and stable compound of formula (9) acid salt with respect to chemical and chiral purities.

To convert the crude compound of formula (9) (partially racemised) to compound of formula (9) acid and to get pure compound of formula (9) acid, which is back esterified to get pure compound of formula (9).

To overcome the problem of partial racemisation during the conversion of compound of formula (8) to compound of formula (9).

To avoid use of highly reactive, difficult to handle and expensive chemicals such as sodium hydride and ethyl iodide and replaced with simple, inexpensive chemicals such as diethylsulphate and potassium carbonate.

Accordingly, the present invention provides an improved process for the preparation 3-aryl-2-hydroxy propanoic acid derivatives of the formula (1) wherein $R^1$ represents hydrogen atom or $(C_1-C_6)$alkyl group such as methyl, ethyl, propyl, isopropyl and the like, and $R^2$ represents $(C_1-C_6)$ alkyl group such as methyl, ethyl, propyl, isopropyl and the like which comprises:

(i). selectively benzylating L-tyrosine of the formula (10) using benzyl chloride, $CuSO_4$ and sodium hydroxide in a solvent to yield a compound of the formula (11), (ii). diazotising the compound of the formula (11) in the presence of an acidic reagent and an organic solvent to produce compound of the formula (8a), (iii). simultaneous etherification and esterification of compound of formula (8a) using alkylating agent in the presence of a base and a solvent to obtain crude compound of formula (9a) with ee>90% wherein $R^1$ represents hydrogen or lower alkyl group and $R^2$ represents lower alkyl group, (iv). hydrolysing the crude compound of formula (9a) obtained in step (iii) above in polar solvents using aqueous alkali to produce compound of formula (9b) acid wherein $R^1$ represents hydrogen or lower alkyl group, (v). treating the compound of formula (9b) acid where $R^1$ represents hydrogen and lower alkyl group with chiral base in the presence of solvent to produce chemical and chiral pure (ee>99%) salt of formula (12) where $R^1$ represents hydrogen or lower alkyl group and X represents chiral bases such as R(+)-α-methylbenzylamine, S(+) phenylglycinol, cinchonidine, ephidrine, N-octylglucaramine, N-methylglucaramine and the like, (vi). if desired, recrystallising compound of formula (12) obtained above in a solvent to produce highly pure compound of formula (12) where $R^1$ represents hydrogen or lower alkyl group, (vii). converting the compound of formula (12) defined above using a solvent and an acid to pure compound of formula (9b) where $R^1$ represents hydrogen or lower alkyl group, (viii). esterifying the pure compound of formula (9b) defined above using alkylating agent in the presence of potassium carbonate, hydrochloric acid, sulfuric acid, amberlite or amberlist to produce pure compound of formula (9c) where $R^1$ represents hydrogen or lower alkyl group and $R^2$ represents lower alkyl group and (ix). debenzylating the compound of formula (9c) using aqueous alcohol in the presence of metal catalysts to yield pure compound of formula, (1) where $R^1$ represents hydrogen or lower alkyl group and $R^2$ represents lower alkyl group.

The process explained above is shown in scheme-5 below:

nitrite, isoamyl nitrite, potassium nitrite, ammonium nitrite and the like under acidic conditions using acids such as sulfuric acid, HCl, acetic acid and the like, in appropriate organic solvent such as $CHCl_3$, 1,4-dioxane, THF, acetone and the like, gives the compound of the formula (8a). Simultaneous etherification and esterification of compound of formula (8a) to obtain crude compound of formula (9a) may be carried out using alkyl sulfates such as diethyl sulphate, dimethylsulphate and the like or alkyl halides such as ethyl iodide, methyliodide and the like, in the presence of solvents such as hydrocarbons like toluene, benzene and the like or DMF, DMSO, MIBK and the like, in alkali bases such as sodium carbonate, potassium carbonate, sodium methoxide, sodium hydride and the like. Alternatively, the compound of formula (9a) may also be prepared by slow addition of compound of formula (8a) to a solution of DMF, sodium hydride, and alkali halides such as methyl iodide, ethyl iodide and the like at a temperature ranging from 0 to 80° C. The compound of formula (9a) upon hydrolysis in polar solvents such as alcohols such as methanol, ethanol, propanol, isopropanol and the like or ketonic solvents such as acetone, methyl ethyl ketone and the like using aqueous alkali bases such as sodium hydroxide or potassium hydroxide yields compound of formula (9b). The resolution of compound of formula (9b) with chiral bases such as R(+)-α-methylbenzylamine, S(+) phenylglycinol, cinchonidine,

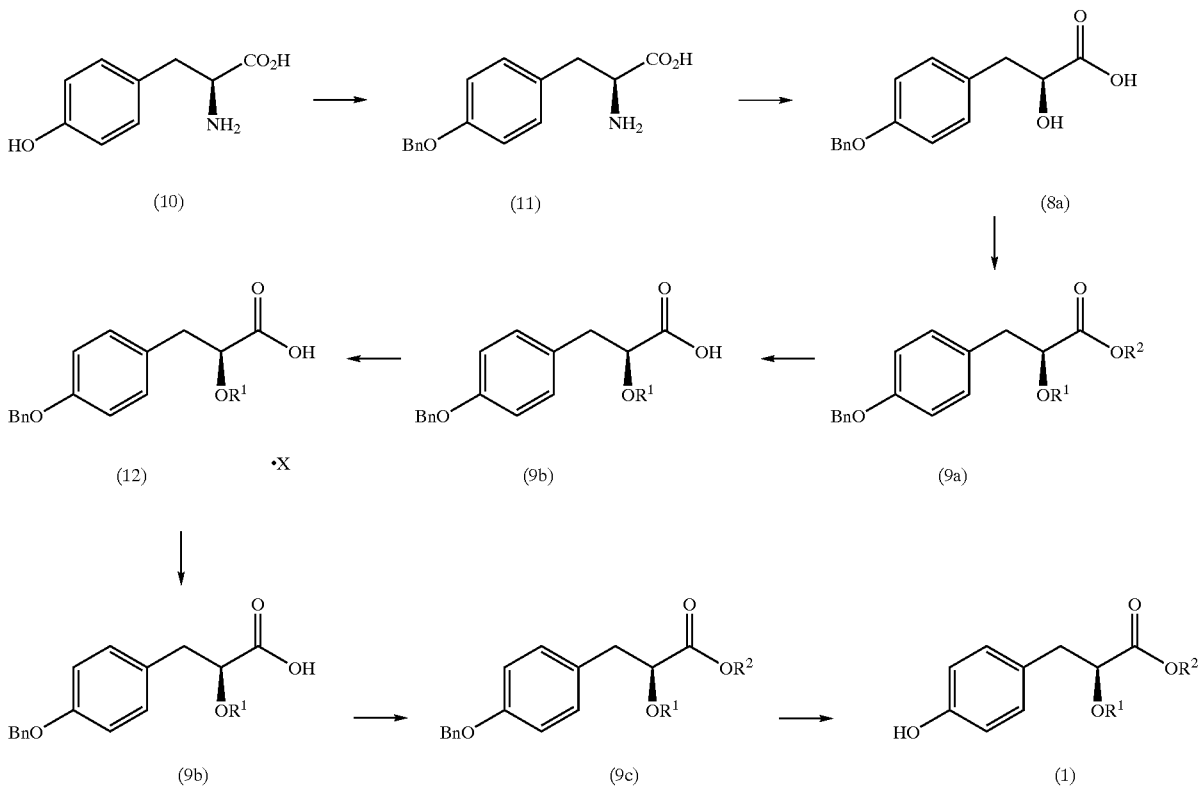

Scheme-5

The process of the present invention starts with benzylating the compound formula (10) using benzyl halide, CuSO4, sodium hydroxide in the presence of solvents such as aqueous methanol, ethanol and the like to afford compound of the formula (11). Diazotization of the compound of the formula (11) using diazotizing agent such as sodium ephidrine, N-octylglucaramine, N-methylglucaramine and the like using solvents such as alkyl ester such as methyl acetate, ethyl acetate, ethyl propanoate, n-butylacetate and the like or alcohol such as methanol, ethanol, propanol, isopropanol and the like or ketone such as acetone, methyl isobutyl ketone and the like or acetonitrile produces the chemical and chiral pure compound of formula (12) where X represents chiral bases such as R(+)-α-methylbenzylamine, S(+) phenylglycinol, cinchonidine, ephidrin, N-octylglucaramine, N-methylglucaramine and the like. The compound of formula (12) defined above may further purified by recrystallization from solvents such as alkyl ester such as methyl acetate, ethyl acetate, ethyl propanoate, n-butylacetate and the like or alcohol such as methanol, ethanol, propanol, isopropanol and the like or ketone such as acetone, methyl ethyl ketone, methyl isobutyl ketone and the like or acetonitrile to obtain highly pure compound of formula (12). The pure compound of formula (9b) is obtained from the compound of formula (12) by treating with acid such as hydrochloric acid, sulfuric acid and the like in the presence of solvent such as toluene and the like. The pure compound of formula (9b) obtained above is esterified with suitable alcohols such as methanol, ethanol, propanol, isopropanol, butanol and the like or alkyl sulfates such as methyl sulfate, ethyl sulfate and the like in the presence of acids such as hydrochloric acid, sulfuric acid and the like or acidic resins such as amberlite, amberlist and the like or bases such as potassium carbonate and the like to produce pure compound of formula (9c). The debenzylation of the compound of formula (9c) using THF, aqueous acetic acid, ethyl acetate, aqueous ($C_1$–$C_6$) alcohols such as aqueous methanol, ethanol, propanol, isopropanol and the like in the presence of metal catalysts such as Pd/C produces pure compound of formula (1).

EXAMPLE 1

Step (i)

Preparation of (S)-2-amino-3-(4-benzyloxyphenyl) propionic acid of the formula (11)

To a solution of L-tyrosine of the formula (10) (250 g) in 2N NaOH solution (552 ml), copper sulphate solution (172 g of $CuSO_4$ in 600 ml of water) was added and heated at 60° C. for 2 h. The reaction mixture was cooled to room temperature and methanol (2.5 L) and 2N NaOH (83 ml) was added and then benzyl chloride (15 ml) was added drop wise. The reaction mass was allowed to warm to room temperature. The precipitate was filtered and washed to give the title compound as white to off-white solid (260 g, 70%) (Ref: *Bodansky & Bodansky* pp50).

Step (ii)

Preparation of S(−)-2-hydroxy-3-(4-benzyloxyphenyl)propionic acid of the formula (8a)

To a stirred solution of (S)-2-amino-3-(4-benzyloxyphenyl)propionic acid of the formula (11) (300 g) obtained according to the procedure described in step (i) above, in acetone (1.8 L) and dilute $H_2SO_4$ (75 ml in 1.2 L of $H_2O$) at 0° C., a solution of $NaNO_2$ (210 g in 400 ml $H_2O$) was added slowly between 0° C. to 15° C. After complete addition of $NaNO_2$ the reaction mixture was maintained below 25° C. for a period of 3 h. The progress of the reaction was monitored by TLC. After completion of the reaction, the reaction mixture was extracted with ethyl acetate. The organic extracts were concentrated and the residue was purified by washing with diisopropyl ether to give the title compound of the formula (8a) as off white to yellowish solid (159 g, 52.8%).

Step (iii)

Preparation of crude S(−) ethyl 2-ethoxy-3-(4-benzyloxyphenyl) propanoate of the formula (9a)

A mixture of S(−) 2-hydroxy-3-(4-benzyloxyphenyl) propionic acid of the formula (8a) (50 g), potassium carbonate (152 g), diethyl sulfate (113 g), and toluene (750 ml) was taken in a round bottom flask and refluxed for 24 to 36 h. The completion of the reaction was monitored by TLC. After completion of the reaction, water (500 ml) was added and stirred to dissolve inorganic salts. Organic layer was concentrated to give crude ethyl 2-ethoxy-3-(4-benzyloxyphenyl) propanoate of the formula (9a) (56 g, 93%).

The other compounds of formula (9a) are also prepared using the solvents given below following the procedure as described above:

| S. No. | $R^1$ and $R^2$ | Reagent | Solvent | Yield |
|---|---|---|---|---|
| 1 | Methyl | DMS | toluene/$K_2CO_3$ | 86% |
| 2 | Methyl | DMs | DMF | 76% |
| 3 | Methyl | NaH/$CH_3I$ | DMF | 90% |
| 4 | Ethyl | DES | DMF | 76% |
| 5 | Ethyl | NaH/$C_2H_5I$ | DMF | 97% |

Step (iv)

Preparation of S(−) 2-ethoxy-3-(4-benzyloxyphenyl) propanoic acid the formula (9b)

To a solution of crude S(−) ethyl 2-ethoxy-3-(4-benzyloxyphenyl)propanoate (180 g) of the formula (9a) obtained in step (iii), in methanol (900 ml) cooled to 10–20° C., sodium hydroxide solution (900 ml) was added slowly. The reaction temperature was raised to 25–30° C. and stirred for 4–6 h. Completion of the reaction was monitored by TLC. After completion of the reaction, water (900 ml) was added and extracted with toluene (2×900 ml) to remove impurities. Aqueous layer was removed and pH was adjusted to 2 and extracted with toluene (2×900 ml). Combined organic layer was washed with water and concentrated to afford the title compound of the formula (9b) (139 g, 84%).

Step (v)

Preparation of (S)-2-ethoxy-3-(4-benzyloxyphenyl) propanoic acid α-methyl benzyl amino salt of the formula (12)

To S(−) 2-ethoxy-3-(4-benzyloxyphenyl)propanoic acid (141 g) the formula (9b) dissolved in ethylacetate (1.4 L), R(+)-α-methylbenzylamine (57 g) was added slowly and stirred for 3–4 h. The precipitated white solid was filtered (recrystallised from ethylacetate 1.5 L if required, to the desired purity) to yield pure (S)-2-ethoxy-3-(4-benzyloxyphenyl)propanoic acid α-methyl benzyl amino salt of the formula (12) (125 g, 63%).

The other compounds of formula (12) are also prepared from S(−) 2-ethoxy-3-(4-benzyloxyphenyl)propanoic acid or S(−) 2-methoxy-3-(4-benzyloxyphenyl)propanoic acid using the chiral bases and solvents given below following the procedure as described above:

| S. No. | 9(b) (18) $R^1$ | Chiral base | Solvent | Yield |
|---|---|---|---|---|
| 1 | Ethyl | R(+)-α-methylbenzylamine | Acetone | 77% |
| 2 | Ethyl | R(+)-α-methylbenzylamine | Isopropyl alcohol | 74% |

-continued

| S. No. | 9(b) (18) R¹ | Chiral base | Solvent | Yield |
|---|---|---|---|---|
| 3 | Ethyl | R(+)-α-methylbenzylamine | acetonitrile | 85% |
| 4 | Ethyl | R(+)-α-methylbenzylamine | n-butyl acetate | 81.5% |
| 5 | Ethyl | R(+)-α-methylbenzylamine | Methyl isobutyl ketone | 74% |
| 6 | Ethyl | phenyl glycinol | Ethyl acetate | 70% |
| 7 | Ethyl | phenyl glycinol | Acetone | 56% |
| 8 | Ethyl | phenyl glycinol | Isopropyl alcohol | 60% |
| 9 | Ethyl | phenyl glycinol | acetonitrile | 62% |
| 10 | Ethyl | phenyl glycinol | n-butyl acetate | 68% |
| 11 | Ethyl | phenyl glycinol | Methyl isobutyl ketone | 59% |
| 12 | Methyl | R(+)-α-methylbenzylamine | Acetone | 75% |
| 13 | Methyl | R(+)-α-methylbenzylamine | Isopropyl alcohol | 72% |
| 14 | Methyl | R(+)-α-methylbenzylamine | Ethyl acetate | 60% |
| 15 | Methyl | phenyl glycinol | Acetone | 55% |
| 16 | Methyl | phenyl glycinol | Isopropyl alcohol | 62% |
| 17 | Methyl | phenyl glycinol | Ethyl acetate | 66% |

Step (vi)

Preparation of (S)-methyl 2-ethoxy-3-(4-benzyloxyphenyl)propanoate of the formula (9c)

A mixture of (S)-2-ethoxy-3-(4-benzyloxyphenyl) propanoic acid α-methyl benzyl amino salt of the formula (12) or (S)-2-ethoxy-3-(4-benzyloxyphenyl) propanoic acid phenyl glycinol salt of the formula (18), (6.7 g) water (70 ml) and toluene (35 ml) was taken in a reaction flask and stirred for 5–10 min. The reaction mass was cooled to 10–15° C. and 25% cold sulfuric acid was added slowly to adjust pH of the reaction mass to 2. Aqueous and organic layers were separated. Aqueous layer was extracted with toluene (35 ml). The combined toluene layers were washed with water (20 ml) and evaporated to yield (S) 2-ethoxy-3-(4-benzyloxyphenyl)propanoic acid the formula (9b) (4 g).

The pure compound of formula (9b) obtained above was dissolved in methanol (35 ml), sulfuric acid (0.4 ml) was added and stirred at refluxing temperature for 12–24 h. Completion of the reaction was monitored by TLC. After completion of the reaction, the reaction mixture was cooled to room temperature, diluted with water (35 ml) and extracted with toluene (2×35 ml). The combined organic layer were washed with 0.5% sodium hydroxide solution (30 ml) and water (50 ml) and concentrated to afford pure tile compound of the formula (9c) (3.5 g, 83%).

The other compounds of formula (9c) from compounds of formula (9b) are also prepared using the solvents given below following the procedure as described above:

| S. No. | R¹ | R² | Solvent | Yield |
|---|---|---|---|---|
| 1 | Ethyl | Ethyl | Ethanol/H₂SO₄ | 81% |
| 2 | Ethyl | Ethyl | DES/K₂CO₃ | 80% |
| 3 | Ethyl | Methyl | DMS/K₂CO₃ | 78% |
| 4 | Ethyl | Isopropyl | Isopropyl alcohol/H₂SO₄ | 84% |
| 5 | Methyl | Ethyl | Ethanol/H₂SO₄ | 80% |
| 6 | Methyl | Ethyl | DES/K₂CO₃ | 76% |
| 7 | Methyl | Methyl | DMS/K₂CO₃ | 74% |
| 8 | Methyl | Isopropyl | Isopropyl alcohol/H₂SO₄ | 82% |
| 9 | Methyl | Methyl | Methanol/H₂SO₄ | 85% |

Step (vii)

Preparation of (S)-methyl 2-ethoxy-3-(4-hydroxyphenyl)propanoate of the formula (1)

A mixture of (S)-methyl 2-ethoxy-3-(4-benzyloxyphenyl) propanoate of the formula (9c) (56 g) in aqueous methanol (300 ml) and slurry of 5% palladium carbon (6 g in 60 ml water) was taken in hydrogenation flask and hydrogenated on Parr shake flask at 60 psi pressure for 6–8 h at room temperature. Completion of the reaction was monitored by TLC. After completion of the reaction, the catalyst was filtered and the filtrate was evaporated to yield tile compound of the formula (1) (39 g, 96%).

The other compounds of formula (1) are also prepared using the solvents given below following the procedure as described above:

| S. No. | R¹ | R² | Solvent | Yield |
|---|---|---|---|---|
| 1 | Ethyl | Isopropyl | Aqueous methanol | 87% |
| 2 | Ethyl | Isopropyl | Aqueous ethanol | 85% |
| 3 | Ethyl | Isopropyl | Aqueous isopropyl alcohol | 92% |
| 4 | Ethyl | Isopropyl | Aqueous acetic acid | 80% |
| 5 | Ethyl | Ethyl | Aqueous methanol | 96% |
| 6 | Ethyl | Ethyl | Aqueous ethanol | 82% |
| 7 | Ethyl | Ethyl | Aqueous isopropyl alcohol | 89% |
| 8 | Ethyl | Ethyl | Aqueous acetic acid | 86% |
| 9 | Methyl | Isopropyl | Aqueous methanol | 92% |
| 10 | Methyl | Isopropyl | Aqueous ethanol | 84% |
| 11 | Methyl | Isopropyl | Aqueous isopropyl alcohol | 90% |
| 12 | Methyl | Isopropyl | Aqueous acetic acid | 88% |

Advantages of the Present Process

An efficient synthesis for the production of compounds of formula (I) with high chiral and chemical purity.

The overall yield of the process has been improved.

Pyrophoirc and exotic reagents like NaH are replaced with simple, inexpensive chemicals such as diethylsulphate and potassium carbonate.

We claim:

1. An improved process for the preparation of a 3-aryl-2-hydroxy propanoic acid derivative of the formula (1)

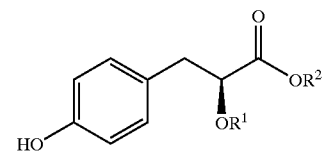

(1)

where R¹ represents hydrogen atom or $(C_1-C_6)$alkyl group and R₂ represents $(C_1-C_6)$alkyl group which comprises:

(i) selectively benzylating L-tyrosine of the formula (10)

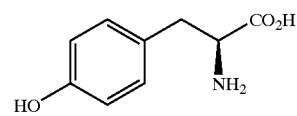

(10)

using benzyl chloride, CuSO₄ and sodium hydroxide in a solvent to yield a compound of the formula (11),

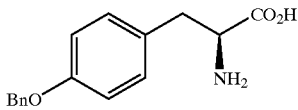

(ii) diazotising the compound of the formula (11) in the presence of an acidic reagent and an organic solvent to produce compound of the formula (8a),

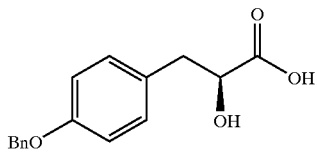

(iii) simultaneously etherifying and esterifying the compound of formula (8a) using an alkylating agent in the presence of a base and a solvent to obtain crude compound of formula (9a) with ee>90%

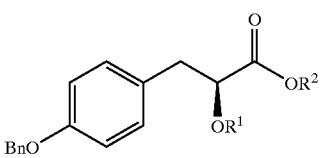

wherein $R^1$ represents hydrogen or lower alkyl group and $R^2$ represents lower alkyl group, (iv) hydrolysing the crude compound of formula (9a) obtained in step (iii) above in a polar solvent using aqueous alkali to produce compound of formula (9b)

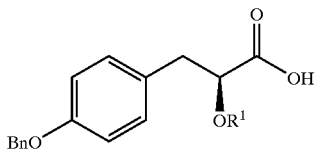

wherein $R^1$ represents hydrogen or lower alkyl group, (v) treating the compound of formula (9b) where $R^1$ represents hydrogen or lower alkyl group with chiral base in the presence of solvent to produce chemically and chirally pure (ee>99%) salt of formula (12)

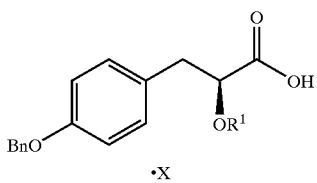

where $R^1$ represents hydrogen or lower alkyl group and X represents a chiral base selected from the group consisting of R(+)-α-methylbenzylamine, S(+) phenylglycinol, cinchonidine, ephidrine, N-octylglucaramine and N-methylglucaramine, (vi) optionally, recrystallising the compound of formula (12) obtained above in a solvent to produce highly pure compound of formula (12) where $R^1$ represents hydrogen or lower alkyl group, (vii) converting the compound of formula (12) defined above using a solvent and an acid to obtain a pure compound of formula (9b),

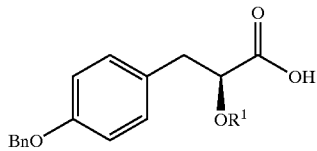

where $R^1$ represents hydrogen or lower alkyl group, (viii) esterifying the pure compound of formula (9b) defined above using an alkylating agent in the presence of potassium carbonate, hydrochloric acid, sulfuric acid, amberlite or amberlist to produce pure compound of formula (9c)

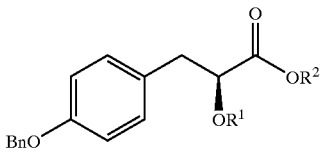

where $R^1$ represents hydrogen or lower alkyl group and $R^2$ represents lower alkyl group and (ix) debenzylating the compound of formula (9c) using THF, aqueous acetic acid, ethyl acetate or an aqueous alcohol in the presence of a metal catalyst to yield pure compound of formula (1) where $R^1$ represents hydrogen or lower alkyl group and $R^2$ represents lower alkyl group.

2. The process as claimed in claim 1, wherein the solvent used for benzylation is selected from aqueous methanol or ethanol.

3. The process as claimed in claim 1, wherein the diazotization of the compound of the formula (11) is carried out using a diazotizing agent selected from the group consisting of sodium nitrite, isoamyl nitrite, potassium nitrite and ammonium nitrite.

4. The process as claimed in claim 1, wherein the diazotization is carried out under acidic conditions using an acid selected from the group consisting of sulfuric acid, HCl and acetic acid.

5. The process as claimed in claim 1, wherein the diazotization is carried out using an organic solvent selected from the group consisting of $CHCl_3$, 1,4-dioxane, THF and acetone.

6. The process as claimed in claim 1, wherein the simultaneous etherification and esterification of compound of formula (8a) is carried out using an alkylating agent selected from the group consisting of dimethyl sulfate, diethyl sulfate, methyliodide and ethyliodide.

7. The process as claimed in claim 1, wherein the solvent used for simultaneous etherification and esterification of compound of formula (8a) is selected from the group consisting of toluene, benzene, DMF, DMSO and MIBK.

8. The process as claimed in claim 1, wherein the base used for simultaneous etherification and esterification of compound of formula (8a) is selected from the group consisting of sodium carbonate, potassium carbonate, sodium methoxide and sodium hydride.

9. The process as claimed in claim 1, wherein the hydrolysis in step (iv) is effected in the presence of a polar solvent selected from the group consisting of methanol, ethanol, propanol, isopropanol, acetone and methyl ethyl ketone.

10. The process as claimed in claim 1, wherein the hydrolysis in step (iv) is effected in the presence of alkali selected from the group consisting of sodium hydroxide and potassium hydroxide.

11. The process as claimed in claim 1, wherein the resolution of compound of formula (9b) is effected using a chiral base selected from the group consisting of R(+)α-methylbenzylamine, S(+)-phenylglycinol, cinchonidine, ephidrine, N-octylglucaramine and N-methylglucaramine.

12. The process as claimed in claim 1, wherein the resolution in the step (v) is effected in the presence of a solvent selected from the group consisting of methyl acetate, ethyl acetate, ethyl propanoate, n-butylacetate, methanol, ethanol, propanol, isopropanol, acetone, methyl isobutyl ketone and acetonitrile.

13. The process as claimed in claim 1, wherein the recrystallization in step (vi) is effected using a solvent selected from the group consisting of methyl acetate, ethyl acetate, ethyl propanoate, n-butylacetate, methanol, ethanol, propanol, isopropanol, acetone, methyl isobutyl ketone and acetonitrile.

14. The process as claimed in claim 1, wherein the conversion of compound of formula (12) is effected using an acid selected from the group consisting of hydrochloric acid and sulfuric acid.

15. The process as claimed in claim 1, wherein the conversion of compound of formula (12) is effected in the presence of toluene.

16. The process as claimed in claim 1, wherein the esterification in step (viii) is carried out using methanol, ethanol, propanol, isopropanol, butanol, dimethyl sulfate or diethyl sulfate.

17. The process as claimed in claim 1, wherein the debenzylation in step (ix) is effected using THF, aqueous acetic acid, ethyl acetate, or a aqueous ($C_1$–$C_6$) alcohols.

18. The process as claimed in claim 1, wherein the debenzylation in step (ix) is effected in the presence of a metal.

19. The method as claimed in claim 18 wherein the catalyst is Pd/C.

20. The process as claimed in claim 17 wherein the alcohol is selected from the group consisting of methanol, ethanol, propanol and isopropanol.

\* \* \* \* \*